US007211697B2

(12) United States Patent
Eble et al.

(10) Patent No.: US 7,211,697 B2
(45) Date of Patent: May 1, 2007

(54) METHOD FOR PRODUCING SPECIFIC CRYSTALLINE MODIFICATIONS OF POLMORPHOUS SUBSTANCES

(75) Inventors: Axel Eble, Köln (DE); Wolfram Sirges, Düsseldorf (DE); Ulrich Schwiedop, Monheim (DE); Armin Heyn, Gladbach (DE)

(73) Assignee: Bayer CropScience AG, Monheim (DE)

( * ) Notice: Subject to any disclaimer, the term of this patent is extended or adjusted under 35 U.S.C. 154(b) by 1 day.

(21) Appl. No.: 10/515,431

(22) PCT Filed: May 23, 2003

(86) PCT No.: PCT/EP03/05395

§ 371 (c)(1),
(2), (4) Date: Jul. 11, 2005

(87) PCT Pub. No.: WO03/099409

PCT Pub. Date: Dec. 4, 2003

(65) Prior Publication Data

US 2006/0036115 A1 Feb. 16, 2006

(30) Foreign Application Priority Data

May 29, 2002 (DE) ................. 102 23 913

(51) Int. Cl.
*C07C 315/99* (2006.01)
(52) U.S. Cl. ........................................ 568/28
(58) Field of Classification Search .................. 568/28
See application file for complete search history.

(56) References Cited

U.S. PATENT DOCUMENTS 4,695,673 A 9/1987 Heather et al. ............. 568/310
5,716,445 A 2/1998 Stirling et al. .............. 106/496
5,939,555 A 8/1999 Foguet et al. ............ 548/311.1
5,959,108 A 9/1999 Bauer et al. ................. 544/291
6,350,871 B1* 2/2002 Sanderson et al. .......... 540/554
6,809,206 B2* 10/2004 Wojtkowski ............. 548/364.4

FOREIGN PATENT DOCUMENTS

| DE | 101 52 459 | 5/2003 |
| EP | 137 963 | 4/2001 |
| WO | 01/10830 | 2/2001 |
| WO | 01/64672 | 9/2001 |

OTHER PUBLICATIONS

Angew. Chem. Int. Ed. 338, (month unavailable) 1999, pp. 3440-3461, J. Bernstein et al, "Concomitant Polymorphs".
J. Pharm. Sci. 58, Aug. 1969, pp. 911-929, J. Haleblian et al, "Journal of Pharmaceutical" Pharmaceutical Applications of Polymorphism.
Powder Technology, 121, (month unavailable) 2001, pp. 46-52, Nicholas Blagden, "Crystal engineering of polymorph appearance: the case of sulphathiazole".
Crystal Growth & Design, vol. 1, No. 1, (month unavailable) 2001, pp. 59-65, R.J. Davey et al, "Crystal Polymorphism as a Probe for Molecular Self-Assembly during Nucleation from Solutions: The Case of 2,6-Dihydroxybenzoic Acid".

* cited by examiner

*Primary Examiner*—Turman Page
*Assistant Examiner*—Chukwuma Nwaonicha
(74) *Attorney, Agent, or Firm*—Richard E. L. Henderson

(57) ABSTRACT

The present invention pertains to a process for the production of a specific crystal modification of a polymorphic, organic substance by precipitation of the specific crystal modification from the aqueous solution of the salt of the polymorphic substances using ordinary water-soluble organic solvents as additives as well as an acid or base.

12 Claims, 2 Drawing Sheets

Wavelength cm⁻¹

ＵＳ 7,211,697 Ｂ2

METHOD FOR PRODUCING SPECIFIC CRYSTALLINE MODIFICATIONS OF POLMORPHOUS SUBSTANCES

RELATED APPLICATIONS

The present patent application has been filed under 35 U.S.C. 371 as a national stage application of PCT/EP03/05375, filed May 23, 2003, which was published in German as International Patent Publication WO 03/099409 on Dec. 4, 2003, which is entitled to the right of priority of German Patent Application 102 23 913.4, filed May 29, 2002.

BACKGROUND OF THE INVENTION

The present invention pertains to a process for the production of a specific crystal modification of a polymorphic, organic substance by precipitation of the specific crystal modification from the aqueous solution of the salt of the polymorphic substances using ordinary water-soluble organic solvents as additives as well as an acid or base.

The polymorphism of active substances is of great importance for chemical development, process development and the development of formulations. It is known that some organic substances occur in only one crystal structure, others (referred to as polymorphs) in two or more structures (known as modifications or crystal modifications). It is not possible to predict the number of crystal modifications, including their physiochemical properties, particularly their thermodynamic stability, as well as the different behavior after administration in living organisms.

It is known that for some polymorphs a particular modification represents the thermodynamically stable phase throughout the entire temperature range up to the melting point, whereas with other material systems there are one or more transition points at which the stability relationship reverses. In a range apart from this transition point, one particular modification is always thermodynamically stable. All other modifications that exist in this range are metastable and transform themselves sooner or later into the thermodynamically stable modifications. The time in which such a conversion takes place is specific to the material and depends on the kinetics of the material system. The material-specific kinetics also determine which modification is formed during a crystallization or precipitation process. It is not possible to predict the stability relationship of co-existent crystal modifications, especially the existence and location of the aforementioned transition points. Furthermore it is neither possible to predict the kinetics of the conversion of metastable modifications to stable ones nor to predict which modification will be formed in a crystallization or precipitation process. A review of the current state of knowledge regarding these fundamental thermodynamic and kinetic relationships is found in J. Bernstein, R. J. Davey. J. O. Henck. Angew. Chem. Int. Ed., 1999, 38, 3440–3461.

It is known that the formation of metastable modifications can be favored, although the driving force for the formation of the thermodynamically stable phase in a crystallization or precipitation process is the greatest. Since time within which a transformation of co-existent crystal modifications takes place is usually orders of magnitude longer than the time for phase formation in a crystallization or precipitation process, these products, which were formed in a metastable structure, typically remain in this state for the time being during the further production and processing steps. Some known examples of this behavior are given in J. Bernstein et al. (see above). Numerous problems can be caused, particularly with active substances, by using or processing metastable crystal modifications. These problems, caused primarily by undesired and uncontrolled crystal growth (recrystallization), can occur during manufacture, formulation, storage, transport or application and can cause significant changes in bioavailability, caking etc. (J. Halebian, W. McCrone, J. Pharm. Sci. 58 (1969) 911).

An example of such problems is 2-(2-chloro-4-mesyl-benzoyl)cycloliexane-1,3-dione hereinafter referred to as sulcotrione, which has herbicide properties and is used in the production of weed-killers. Sulcotrione occurs for example in two modifications (in this regard, refer to the German patent application no. 10152459.5, which as a whole is to be part of the present application). The metastable modification, hereinafter referred to as modification (I), is the product of a manufacturing process, which follows the description in EP-A2-0 186 117. Since this modification is metastable, it is less suitable for production, formulation, storage and application of this active substance than the stable modification.

Commonly applied methods for reproducible manufacture of the stable modification of a substance are evaporative or cooling crystallization, as well as recrystallization in a carefully selected solvent (see WO 97/49681 A1). The choice of an appropriate solvent is made with the objective of influencing the surface energy of the crystal with the surrounding solution and/or the complex formation of the molecules in the course of the crystallization in order to promote formation of the desired crystal structure (N. Bladgeni. Powder Technology, 121 (2001) 46–52; R. J. Davey et al., Crystal Growth & Design, 1(1), (2001) 59–65; U.S. Pat. No. 5,959,108; U.S. Pat. No. 5,939,555). In WO 01/64672 A1 for example, a process is described for obtaining a specific modification. It is based on the solution of the isomorph in butanone/water (10:1) with subsequent addition of an acid. The disadvantage of such strategies is that a solvent for crystallization found in this manner is only seldom suitable for the preceding process and reaction steps. Consequences of this are cost-intensive measures such as changing the solvent, or recrystallization of an already formed metastable crystal structure is necessary. In particular, such procedures are also usually associated with a significant loss of yield.

Another known method to have a targeted influence on the formation of specific crystal structures of a polymorphic substance is the use of so-called "tailor-made" additives (E. Staab et al., Adv. Mater., 2 (1990) 40). The objective of such "tailor-made" additives is likewise to influence the surface energy of the crystal with respect to the surrounding solution and/or the formation of molecular complexes during crystallization in order to promote the formation of the desired crystal structure (see for example U.S. Pat. No. 5,716,445 A). Characteristic of "tailor-made" additives is a partial conformance or similarity of the molecular structure to that of the polymorphic substance. The advantage of using such "tailor-made" additives compared to the aforementioned strategy is the possibility of use in different solvents, which makes the implementation of such a process simpler. However, as a rule the specifically designed additives must be synthesized exclusively for their use to exercise specific influence on the polymorphism, which makes their development time-consuming and makes the process in which they are used expensive.

It was therefore the task of the present invention to prepare a process for the manufacture of specific modifications that can be used for efficient, cost-effective recovery of specific modifications. In particular it was the task of the present invention to make available a process for obtaining the modification that does not require a change of solvent and/or recrystallization.

The challenge was solved in the present invention by using inexpensive and easy-to-use additives in order to achieve the formation of a specific crystal modification. These additives also show their effect in solvents used in the prior reactions and processing steps, so that a change of solvent and/or additional process steps can be omitted.

It was found that typical organic solvent molecules are outstandingly suitable additives for promoting the formation of specific crystal structures of organic polymorphic substances in acid/base precipitative crystallizations. Surprisingly, the production of specific modifications of polymorphic organic substances succeeds directly by precipitation of the specific crystal modification from the salt of the polymorphic substance in aqueous solution according to the following reaction equation,

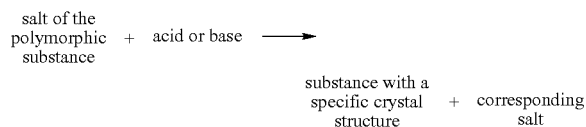

whereby the precipitation of the substance in the desired crystal structure is promoted by addition of typical organic, water-soluble solvents as additives.

The term "additive" as it is used here refers to compounds or substances that are added to an existing solution of a substance, whereby the amount (w/w) of the additive applied is preferably less than the amount of substance present in solution. Preferably the additive in an amount that is 0.1 to 20% with respect to the amount of the substance to be precipitated; particularly preferable is an amount of 1 to 10% and especially of 1 to 5%. It does not matter here whether the additive is added to the available solution or whether said solution is added to an available additive or a solution containing the additive.

SUMMARY OF THE INVENTION

Therefore the subject of the present invention is a process for producing a specific crystal modification of a polymorphic substance by precipitations of the specific crystal modification from a salt of the polymorphic substance present in an aqueous solution in the presence of an acid or base and a water-soluble organic solvent.

DESCRIPTION OF THE INVENTION

Figure 1:
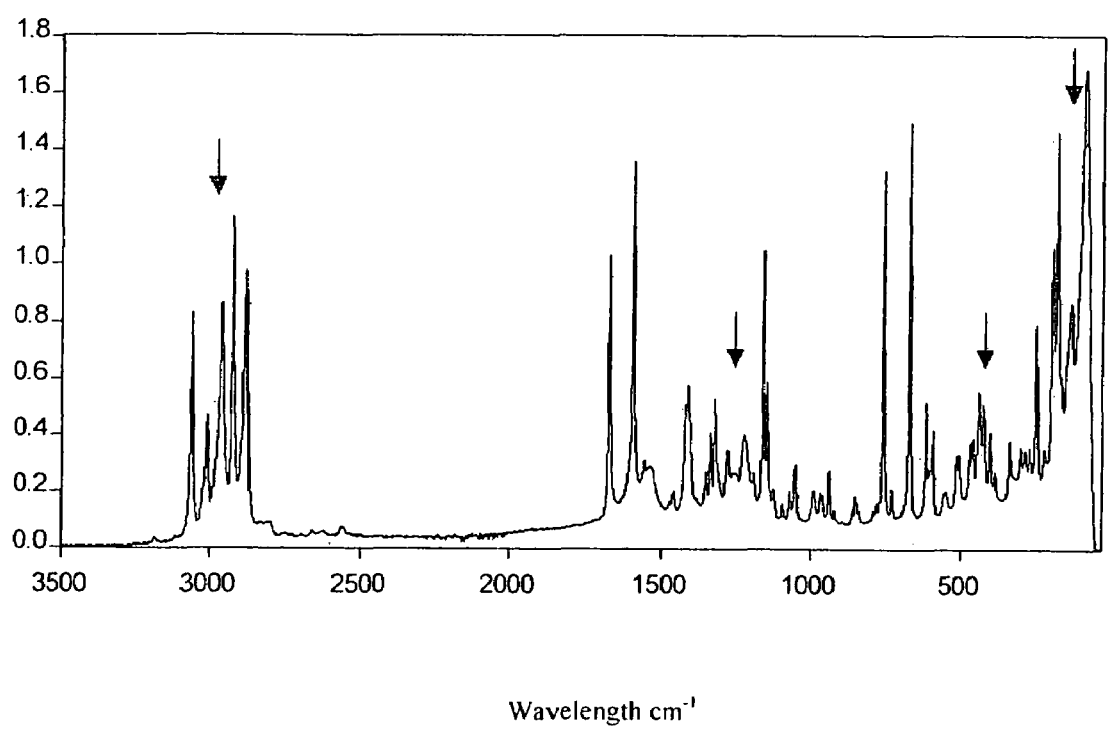
FIG. 1 shows the Raman spectrum of crystal modification I of sulcotrione.
Figure 2:
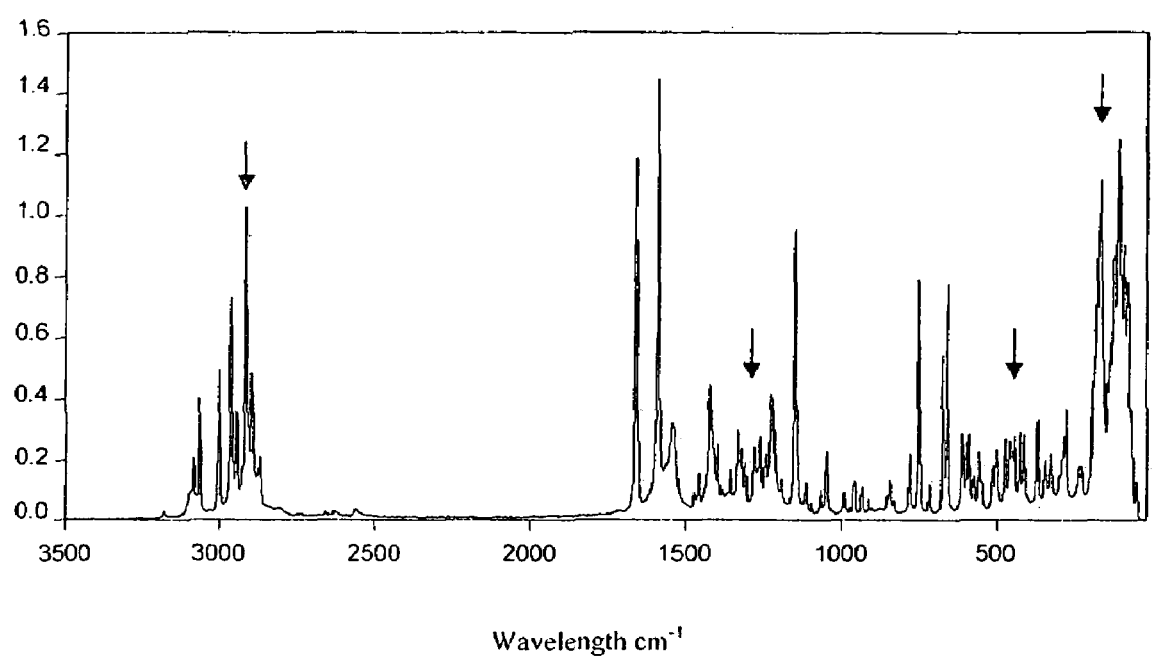
FIG. 2 shows the Raman spectrum of crystal modification II of sulcotrione.

Acids and bases that can be used in the process according to the invention are strong acids or bases typically used in organic chemistry. Usable acids include, for example, HCl, $H_2SO_4$, $HNO_3$ or HF. Usable bases include, for example, NaOH, $Ba(OH)_2$, $Ca(OH)_2$ or KOH.

Organic water-soluble solvents that can be used as additives in this process for specific formation of the desired modification are, among others, short-chain alcohols, such as methanol, ethanol or 2-propanol, short-chain ketones, such as acetone or 2-butanone, carboxylic acids with one to four carbon atoms, such as acetic acid, ethers such as diethyl ether, tetrahydrofuran or methyl t-butyl ether, esters such as methyl acetate, ethyl acetate or methyl formate, heterocyclic amines such as pyridine, formamide, such as dimethyl formamide or even N-methyl pyrrolidone or dimethyl sulfoxide. The term lower or short-chain alcohols is used here to refer to those alcohols having one to ten carbon atoms, preferably one to five carbon atoms. The term lower or short-chain ketones is used here to refer to those ketones having three to ten carbon atoms, preferably three to five carbon atoms.

The mechanism of action of these additives, which promote the formation of kinetically unfavorable modifications, consists therein, that they establish a range of supersaturation in which the desired modifications can be produced. If this range is exceeded by excessive supersaturation, the kinetically preferred modifications will appear again. Therefore in addition to or in combination with the use of water-soluble organic solvent as additives, a precipitative crystallization with controlled supersaturation is also part of this invention. Thus the subject of the invention is a process for producing a specific crystal modification of a polymorphic substance by precipitations of the specific crystal modification from a salt of the polymorphic substance present in an aqueous solution at low supersaturation in the presence of an acid or base and a water-soluble organic solvent.

The precipitative crystallization can be performed by adding a corresponding (equinormal) quantity of an acid/base to a stirred reaction vessel in which the aqueous solution of the salt of the active substance is present together with the additive. A small excess of the acid or base will be added to reach the target pH value. Seed crystals of the desired modification are added as needed when the solution is slightly supersaturated.

Therefore the subject of the present invention in particular is a process for producing a specific crystal modification of a polymorphic substance as described above by adding the acid or base to a mixture of the aqueous solution of the salt of the polymorphic substance and a suitable additive as well as seed crystals if needed.

The precipitative crystallization can likewise be carried out by adding the aqueous solution of the salt of the polymorphic substance to a mixture of the corresponding quantity of an acid or base and a suitable additive as well as seed crystals of the desired modification if needed.

It is preferred to carry out the precipitative crystallization by adding the aqueous solution of the salt of the polymorphic substance and a corresponding quantity of an acid/base in parallel and uniformly with stirring to the aqueous solution of the additive and seed crystals of the desired modification if needed. The addition of each of the added components takes place in such a way that the pH value of the reaction mixture in always kept constant.

The pH value used in the inventive process depends on the particular polymorphic substance or its associated specific modification and can be varied over a relatively large range. The optimal pH value for a precipitation can be determined simply by measuring the yield of the inventive process at various pH values and choosing the pH value with the largest possible yield.

The amount of the inventive additive used in the inventive process can be varied over a larger range. Less than ten percent (w/w) of the additives in relation to the yield of precipitated substance is preferred for use, particularly preferred is less than one percent. However, the additive can also be added in quantities greater than ten percent.

The amount of seed crystals, which are used as necessary in the inventive process, can likewise be varied over a larger range. Less than ten percent (w/w) in relation to the yield of precipitated substance is preferred for use, particularly preferred is less than one percent. However, more than ten percent can also be added. The process can also be carried out without the addition of seed crystals if the additive is efficient enough.

It is preferred to carry out the process at normal pressure and temperatures below 100° C. Temperatures at which the particular desired crystal modification constitutes the stable form have proven especially suitable. The suitable temperature or transition points of the desired, specific crystal modification with each of the other existing modifications can be determined in the manner known to practitioners of the art. The transition point is the temperature at which two crystalline phases of a substance are in equilibrium at a given pressure. For the determination of the transition points between two known modifications, for example the solubility of both modifications can be determined separately from one another as a function of temperature in some appropriate solvent. Intercept points of the solubility curves of two modifications in a solvent at a given pressure indicate the temperature at which a transition point occurs in the stability relationship of both modifications. Particularly suitable in the inventive process is the use of temperatures that are more than 10° C. removed from transition points of the desired crystal modification with each other existing modification, whereby temperatures that are farthest from all transition points of the desired crystal modification with each other existing modification are particularly preferred. The process can also be carried out at pressures other than normal pressure and at temperatures above 100° C.

The addition rate at which the acid/base or the aqueous solution of the salt of the polymorphic substance or both can be added to the reaction mixture while stirring depends on the kinetics of the material system, the concentration of the reagent solutions, the quantity of seed crystals and the effectiveness of the additive used. However, the rate of addition can be varied over a larger range and a favorable rate determined in a simple manner. Here it is important to select the rate of addition in such a way that especially at the beginning of addition, for example of the aqueous solution of the salt of the polymorphic substance to the available acid or base, no uncontrolled supersaturation (supersaturation peaks) occur. Control of the precipitation is facilitated by stirring of the mixture.

The procedure can be used for any polymorphic organic compound that is characterized by one or more dissociating or associating proton, such as weak acids or weak bases. Suitable compounds are therefore characterized in that their solubility in aqueous solution changes with the pH value of the solution.

The difference in solubility between a compound and its salt will ideally span more than two orders of magnitude. Thus at an optimal pH value as described above the solubility of the salt of the polymorphic starting compound should preferably be greater than ten weight percent, more preferably twenty weight percent and most preferably greater than thirty weight percent, while the solubility of the desired specific crystal modification ideally will be less than five weight percent, more preferably less than one weight percent and most preferably less than 0.1 weight percent.

The process is particularly suitable for substances, characterized by a change in solubility in aqueous solution in the range 0<pH<14, particularly in the range 1<pH<13. Such organic substances can be all manner of active substances, such as those used in the pharmaceutical area or in pest management.

Thus in the example of sulcotrione cited above the precipitation of modification II from the sodium enolate of sulcotrione can be achieved using the inventive process with addition of hydrochloric acid.

The subject of the present procedure is therefore also a process for production of modification II of sulcotrione, which is carried out as described above.

As described above, in addition to the sodium ion, any other corresponding base can be used here for the enolate anion according to the inventive process. Likewise the process can be carried out with any other corresponding acid beside the designated hydrochloric acid. The process can also rely on precipitation of a base from its salt by addition of a stronger base. The chosen example of sulcotrione, in which the precipitation of an acid from its salt takes place by addition of a stronger acid, is thus not to be construed as limiting the scope.

In the case of the selected example sulcotrione for example, a temperature of 12° C. is suitable for precipitation of modification II, because temperature is sufficiently far from the transition points and modification II represents the stable modification in this temperature range. Heterocyclic amines, like short-chain alcohols, also prove to be extremely efficient additives for promoting the formation of modification II. Compared to a process without the addition of additives even long-chain alcohols such as dodecanol are suitable for promoting the formation of modification II, however they are less effective. Similarly, the aforementioned esters and ethers, particularly ethyl acetate, tetrahydrofuran and methyl t-butyl ether as well as N-methyl pyrrolidone show a positive effect on the formation of modification II, whereby however their activity is somewhat less compared to the short-chain alcohols and ketones as well as the heterocyclic amines.

In the production of modification II of sulcotrione for example, the parallel addition of aqueous sodium enolate solution and hydrochloric acid at constant pH gave the best results. Possible addition of seed crystals takes place preferably if the solution becomes supersaturated. A pH value of 2.7 was chosen for parallel addition, because the yield is optimal at this pH value. Since the influence of mixing is very important in precipitative crystallization, as described above, care must be exercised that the power input of the stirrer is kept constant despite a sharply increasing filling volume in the chosen reaction vessel. A moderate power input of about 0.15 W/kg with an impeller combined with addition of both reagents at opposing sides of the surface provides ideal conditions for avoiding local supersaturation peaks.

EXAMPLES

Example 1

Production of the Stable Crystal Structure (Modification II) of 2-(2-chloro-4-mesyl-benzoyl)cyclohexane-1,3-dione (sulcotrione) by Direct Precipitation (Additive: heterocyclic amine).

A toluene suspension of the triethylamine salt of 2-(2-chloro-4-mesyl-benzoyl)cyclohexane-1,3-dione is attained by a rearrangement of the corresponding enol ester 3-oxo-cyclohex-1-enyl-(2-chloro-4-mesyl-benzoate) (see EP-A2-186 117). The enol ester is synthesized here by coupling 0.2 mol 2-chloro-4-mesyl-benzoyl chloride with an equimolar quantity of cyclohexane-1,3-dione in toluene in the presence of an excess of triethylamine as a base. This toluene suspension is brought in contact with 500 g of dilute sodium hydroxide (4 weight percent) at 45° C. for 30 minutes in order to obtain the product as the sodium salt dissolved in the aqueous phase and free of byproducts. After phase separation, the aqueous sodium enolate solution is kept at 45° C. The formation of the stable crystal structure (modification II) of the triketone per se by precipitation of this aqueous sodium enolate solution with hydrochloric acid requires a suitable additive, since the formation of the metastable phase (modification I) is favored kinetically in the aqueous system. For this reason, 5 g pyridine together with 90 g distilled water and 15 g seed crystals of modification II (specific surface area >0.75 m²/g) are placed in a reaction vessel, stirred with an impeller at a specific power input of about 0.15 W/kg and equilibrated at 12° C. After the pH value of this sample is adjusted to pH=2.7 with hydrochloric acid, the aqueous sodium enolate solution is added carefully dropwise to this suspension at a rate of 1 g per minute, during which the pH value is kept constant at pH=2.7 by controlled addition of 37 weight percent hydrochloric acid, the temperature remaining constant at 12° C. and the power input from the stirrer kept constant at 0.15 W/kg. The two reagent solutions are dripped onto the surface from opposing sides. The product obtained in this manner is filtered and dried under vacuum at a temperature of 50° C. Raman spectroscopy of the product shows the following peaks in [cm$^{-1}$]:

3175, 3096, 3083, 3067, 3002, 2965, 2948, 2918, 2900, 2874, 1660, 1589, 1543, 1458, 1422, 1397, 1358, 1337, 1322, 1310, 1283, 1266, 1247, 1228, 1152, 1117, 1050, 992, 958, 935, 845, 779, 752, 718, 676, 660, 613, 594, 578, 560, 513, 503, 476, 460, 447, 429, 415, 371, 346, 328, 280, 236, 227, which match those of the stable modification II (see German patent application no. 10152459.5).

Example 2

Production of the Stable Crystal Structure (Modification II) of 2-(2-chloro-4-mesyl-benzoyl)cyclohexane-1,3-dione (sulcotrione) by Direct Precipitation (Additive: ketone).

The procedure described in Example 1 was carried out in an analogous manner with ketones as an additive in order to obtain 2-(2-chloro-4-mesyl-benzoyl)cyclohexane-1,3-dione in its stable crystal structure (modification II) directly by precipitative crystallization from the corresponding aqueous sodium enolate solution. The crystal structure obtained in this manner was characterized based on the characteristic Raman spectrum as presented in Example 1. The ketones used, the quantities used and the result of the process are in given in Table I.

TABLE I

| Example | Additive | Additive Quantity in Grams | Crystal Structure |
|---------|----------|----------------------------|-------------------|
| 2(A) | acetone | 5 | Mod. II |
| 2(B) | 2-butanone | 5 | Mod. II |

Example 3

Production of the Stable Crystal Structure (Modification II) of 2-(2-chloro-4-mesyl-benzoyl)cyclohexane-1,3-dione (sulcotrione) by Direct Precipitation (Additive: Alcohols).

The procedure described in Example 1 was carried out in an analogous manner with various alcohols as an additive in order to obtain 2-(2-chloro-4-mesyl-benzoyl)cyclohexane-1,3-dionie in its stable crystal structure (modification II) directly by precipitative crystallization from the corresponding aqueous sodium enolate solution. The crystal structure obtained in this manner was characterized based on the characteristic Ramaan spectrum as presented in Example 1. The alcohols used, the quantities used and the result of the process are in given in Table II.

TABLE II

| Example | Additive | Additive Quantity in Grams | Crystal Structure |
|---------|----------|----------------------------|-------------------|
| 3(A) | methanol | 5 | Mod. II |
| 3(B) | ethanol | 5 | Mod. II |
| 3(C) | 2-propanol | 5 | Mod. II |

Example 4

Production of the Stable Crystal Structure (Modification II) of 2-(2-chloro-4-mesyl-benzoyl)cyclohexane-1,3-dione (sulcotrione) by Direct Precipitation with Low Amounts of Additive.

The process described in Example 3 (additive: ethanol) was performed in a similar manner to obtain 2-(2-chloro-4-mesyl-benzoyl)cyclohexane-1,3-dione in its stable crystal structure (modification II) directly by precipitative crystallization from the corresponding aqueous sodium enolate solution, but with the quantities of ethanol shown in Table III. The crystal structure obtained in this manner was characterized based on the characteristic Raman spectrum as presented in Example 1. The quantities use as well as the result of the experiment are given in Table III.

TABLE III

| Example | Additive | Additive Quantity in Grams | Crystal Structure |
|---------|----------|----------------------------|-------------------|
| 4(A) | ethanol | 2.2 | Mod. II |
| 4(B) | ethanol | 0.5 | Mod. II |

Example 5

Reducing the Addition Time by Increasing the Amount of Additive (250 g Methanol).

The aqueous sodium enolate solution of 2-(2-chloro-4-mesyl-benzoyl)cyclohexane-1,3-dione is produced in the manner described in Example 1. In order to obtain the stable crystal structure (modification II) of the triketone with the shortest addition times, 250 g methanol and 22 g seed crystals of modification II (specific surface area >0.75 m²/g) are placed in a reaction vessel, stirred with an impeller at a specific power input of about 0.15 W/kg and equilibrated at 12° C. After the pH value of this sample was adjusted to pH=2.7 with hydrochloric acid, the aqueous sodium enolate solution is added carefully dropwise to this suspension at a rate of 4 g per minute, during which the pH value is kept constant at pH=2.7 by controlled addition of 37 weight percent hydrochloric acid, the temperature remaining constant at 12° C. and the power input from the stirrer kept constant at 0.15 W/kg. The two reagent solutions are dripped onto the surface opposite each other. The product obtained in this manner is filtered and dried under vacuum at a temperature of 50° C. The Raman spectrum presented in Example 1 indicates the product obtained in this manner to be modification II.

Example 6

Reduction of the Addition Times for Precipitation of the Stable Crystal Modification with Low Quantities of Additives by Using Dispersion Equipment.

The aqueous sodium enolate solution of 2-(2-chloro-4-mesyl-benzoyl)cyclohexane-1,3-dione is produced in the manner described in Example 1. In order to recover the stable crystal structure (modification II) of the triketone with shorter addition times, 5 g pyridine. 90 g distilled water and 15 g seed crystals of the modification II are placed in a reaction vessel and the pH value is adjusted to pH=2.7 with hydrochloric acid. This suspension is thereupon treated for two minutes with a dispersion machine. After this treatment, the suspension is stirred with an impeller at a specific power input of about 0.15 W/kg and equilibrated at 12° C. before the aqueous sodium enolate solution is added carefully dropwise to this suspension at a rate of 2.5 g per minute, during which the pH value is kept constant at pH=2.7 by controlled addition of 37 weight percent hydrochloric acid constant, the temperature constant at 12° C. and the power input by the stirrer constant at 0.15 W/kg. The two reagent solutions are dripped onto the surface from opposing sides. After 320 g of the aqueous sodium enolate solution has been added, the suspension is treated for another five minutes with the dispersion machine. Then the addition of the aqueous sodium enolate solution is completed at a rate of 2.5 g per minute at constant temperature and constant pH. The product obtained in this manner is filtered and dried under vacuum at a temperature of 50° C. The Raman spectrum presented in Example 1 indicates the product obtained in this manner to be modification II.

What is claimed is:

1. A process for the production of a specific crystal modification of 2-(2-chloro-4-mesyl-benzoyl)-cyclohexane-1,3-dione comprising precipitating the specific crystal modification from an aqueous solution of a salt of 2-(2-chloro-4-mesyl-benzoyl)cyclohexane-1,3-dione with an acid or base in the presence of a water-soluble organic solvent selected from the group consisting of ketones and alcohols and mixtures thereof.

2. A process according to claim 1 additionally comprising adding seed crystals of the specific crystal modification when the solution is supersaturated.

3. A process according to claim 1 comprising adding the acid or base to an existing mixture of the aqueous solution of the salt of 2-(2-chloro-4-mesyl-benzoyl)cyclohexane-1,3-dione, the additive, and optional seed crystals.

4. A process according to claim 1 comprising adding the aqueous solution of the salt of 2-(2-chloro-4-mesyl-benzoyl)cyclohexane-1,3-dione to an existing mixture of acid or base, the additive, and optional seed crystals.

5. A process according to claim 1 comprising steadily adding the aqueous solution of the salt of 2-(2-chloro-4-mesyl-benzoyl)cyclohexane-1,3-dione and the acid or base at the same time with stirring to an existing mixture of the aqueous solution of an additive, optionally in the presence of seed crystals.

6. A process according to claim 1 in which the pH value is kept at about pH 2.7.

7. A process according to claim 1 in which the organic solvent is an alcohol with 1 to 10 carbon atoms, a ketone with 3 to 10 carbon atoms, or a mixture thereof.

8. A process according to claim 1 in which the acid or base is used in an amount equinormal to the salt of 2-(2-chloro-4-mesyl-benzoyl)cyclohexane-1,3-dione.

9. A process according to claim 1 in which the amount (w/w) of the organic solvent is less than 10% of the amount of the crystal modification of 2-(2-chloro-4-mesyl-benzoyl)cyclohexane-1,3-dione to be precipitated.

10. A process according to claim 1 carried out at a temperature at which the desired crystal modification is the stable form.

11. A process according to claim 1 in which the arrangement of the dosing locations for the reagents and/or the power input from the stirrer ensures mixing that avoids local supersaturation peaks.

12. A process according to claim 1 in which the organic solvent is acetone, 2-butanone, methanol, ethanol, 2-propanol, or a mixture thereof.

* * * * *